United States Patent
Terada et al.

(10) Patent No.: US 9,423,388 B2
(45) Date of Patent: Aug. 23, 2016

(54) PARTICLE ANALYZING DEVICE

(71) Applicant: Hitachi, Ltd., Chiyoda-ku, Tokyo (JP)

(72) Inventors: Koichi Terada, Tokyo (JP); Masakazu Sugaya, Tokyo (JP); Hideo Kashima, Tokyo (JP); Hisashi Nagano, Tokyo (JP); Yasuaki Takada, Tokyo (JP); Hiromi Satou, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/768,926

(22) PCT Filed: Oct. 28, 2013

(86) PCT No.: PCT/JP2013/079102
§ 371 (c)(1),
(2) Date: Aug. 19, 2015

(87) PCT Pub. No.: WO2014/132487
PCT Pub. Date: Sep. 4, 2014

(65) Prior Publication Data
US 2015/0377851 A1    Dec. 31, 2015

(30) Foreign Application Priority Data

Feb. 27, 2013  (JP) ................... 2013-037736

(51) Int. Cl.
*G01N 1/02*  (2006.01)
*G01T 7/02*  (2006.01)
(Continued)

(52) U.S. Cl.
CPC .......... *G01N 33/0057* (2013.01); *G01N 1/2202* (2013.01); *G01N 1/2273* (2013.01); *G01N 15/00* (2013.01); *G01N 2001/022* (2013.01)

(58) Field of Classification Search
CPC . G01N 1/2214; G01N 1/2205; G01N 1/2273; G01N 1/405; G01N 1/22; G01N 1/2202; G01N 1/4005; G01N 1/4022; G01N 30/88; G01N 33/0011; G01N 33/0057; G01N 33/227; H01J 49/0422; H01J 49/049; H01J 49/0468; H01J 49/004; B01D 46/10; B01D 46/0006; Y10T 436/11; Y10T 436/114165; B01L 3/502
USPC ............ 73/23.2, 863.23, 31.07, 23.31, 23.41, 73/863.25, 863.81; 250/288, 281, 282, 250/287, 284, 286, 289, 425, 440.11, 250/442.11; 422/88, 93; 436/156, 48
See application file for complete search history.

(56) References Cited

U.S. PATENT DOCUMENTS 3,925,022 A * 12/1975 Showalter .......... G01N 33/0045
422/88
4,069,018 A * 1/1978 Karna ................ G01N 33/0031
340/579

(Continued)

FOREIGN PATENT DOCUMENTS

CA    2012030 A1    9/1991
JP    5-506303 A    9/1993
(Continued)

OTHER PUBLICATIONS

International Search Report (PCT/ISA/210) dated Jan. 21, 2014 with English translation (five pages).

*Primary Examiner* — David A Vanore
(74) *Attorney, Agent, or Firm* — Crowell & Moring LLP

(57) ABSTRACT

An explosive detection apparatus capable of maintaining high availability even in an environment containing a large amount of foreign substances is achieved. The explosive detection apparatus includes means for sequentially replacing a plurality of collection thermal vaporization filters 2 for collecting, heating, vaporizing particles, which have been prepared in advance. The explosive detection apparatus also includes a preheating unit 52 for preheating an unused filter, and sealing is performed by a seal portion between the plurality of filters.

15 Claims, 15 Drawing Sheets

(51) Int. Cl.
*G01N 1/22* (2006.01)
*G01N 33/00* (2006.01)
*G01N 15/00* (2006.01)

(56) References Cited

U.S. PATENT DOCUMENTS

| | | | | |
|---|---|---|---|---|
| 4,202,200 A | * | 5/1980 | Ellson | G01N 1/26 73/31.05 |
| 4,426,214 A | * | 1/1984 | Vandrish | B01D 46/10 55/481 |
| 4,909,090 A | * | 3/1990 | McGown | G01N 1/2214 73/863.12 |
| 5,345,809 A | * | 9/1994 | Corrigan | G01N 1/2214 250/286 |
| 5,915,268 A | * | 6/1999 | Linker | G01N 1/24 422/93 |
| 6,192,766 B1 | * | 2/2001 | Gangrdhagen | G01N 1/24 73/863.12 |
| 6,391,077 B1 | * | 5/2002 | Kudoh | F01N 3/0222 210/510.1 |
| 6,844,546 B2 | * | 1/2005 | Nagano | H01J 49/0031 250/281 |
| 6,884,997 B2 | * | 4/2005 | Kashima | H01J 49/049 250/281 |
| 7,113,277 B2 | * | 9/2006 | Craig | G01N 15/0637 356/317 |
| 7,194,924 B2 | * | 3/2007 | Wisniewski | G01N 1/2202 73/863.21 |
| 7,299,709 B1 | * | 11/2007 | Grove | G01N 1/2273 73/863.11 |
| 7,299,710 B2 | * | 11/2007 | Syage | G01N 1/2205 73/28.04 |
| 7,468,672 B2 | * | 12/2008 | Harden | G01N 27/622 340/573.1 |
| 7,819,028 B2 | * | 10/2010 | Christie | B01L 3/502 73/863.23 |
| 8,171,810 B1 | * | 5/2012 | Sagi-Dolev | G01V 5/0008 340/521 |
| 8,186,234 B2 | * | 5/2012 | Syage | G01N 1/2205 73/29.05 |
| 8,846,407 B2 | * | 9/2014 | Hargrove | G01N 33/0057 422/83 |
| 2003/0012698 A1 | | 1/2003 | Hirota et al. | |
| 2004/0035186 A1 | * | 2/2004 | Allen | G01N 1/2214 73/31.03 |
| 2004/0124352 A1 | * | 7/2004 | Kashima | H01J 49/049 250/288 |
| 2004/0195499 A1 | * | 10/2004 | Ishikawa | G01N 1/2214 250/281 |
| 2005/0058575 A1 | * | 3/2005 | Ishikawa | G01N 1/2214 422/83 |
| 2007/0277626 A1 | * | 12/2007 | Saitoh | B01D 46/0002 73/863.23 |
| 2012/0139736 A1 | * | 6/2012 | Suzuki | H01J 49/0422 340/632 |
| 2014/0238106 A1 | * | 8/2014 | Kashima | G01N 33/0011 73/23.2 |
| 2015/0136975 A1 | * | 5/2015 | Sugaya | H01J 49/0422 250/288 |
| 2015/0235831 A1 | * | 8/2015 | Nagano | G01N 1/2211 73/863.11 |

FOREIGN PATENT DOCUMENTS

| | | |
|---|---|---|
| JP | 7-6729 A | 1/1995 |
| JP | 7-243950 A | 9/1995 |
| JP | 2002-196010 A | 7/2002 |
| JP | 2004-301749 A | 10/2004 |

* cited by examiner

Cross-section A-A'

PARTICLE ANALYZING DEVICE

TECHNICAL FIELD

The present invention relates to a particle analyzing apparatus for collecting and analyzing particles.

BACKGROUND ART

Recently the threat of terrorism has increased worldwide, and, since a method of producing explosives using daily goods has been widely known, terrorism and crimes using explosives are becoming a threat in daily life as well. In London, simultaneous terrorist attacks were committed at subways and buses, resulting in many deaths and injuries. According to the news release, a suspect attempting a suicide attack in a commuter train was arrested in Japan as well. In view of this, conventionally, technologies for limiting carriage of explosives to airplanes or airport facilities have been widely developed.

As a dangerous substance detection technology that has been conventionally developed, for example, an explosive detection apparatus using a mass spectrometer is known. This apparatus determines presence or absence of dangerous substances by sampling explosive vapor leaking from a luggage with the use of a sampling probe, ionizing the explosive vapor with the use of negative corona discharge, and detecting the ionized explosive vapor with the use of the mass spectrometer. Further, there is also known a method for analyzing explosive particles with the use of an analyzer by collecting the explosive particles in a disk-shaped filter, moving the explosive particles to another position, and heating and vaporizing the collected explosive particles.

PTL 1, which is not for explosive particles, discloses a method for automatically attaching/detaching a filter for collecting particles and collecting the filter which has collected the particles in another apparatus by remote control.

CITATION LIST

Patent Literature

PTL 1: JP-A-7-243950

SUMMARY OF INVENTION

Technical Problems

However, conventional technologies have the following problems.

The conventional explosive detection apparatus using the mass spectrometer needs to sample explosive vapor leaking from a luggage with the use of the sampling probe. For destructive explosives or propellant for military use and industrial explosives used in construction sites or the like, stable substances are used for safety operation, and therefore those substances usually have a relatively lower vapor pressure. Thus, instead of sampling vapor, it is necessary to collect and analyze particles.

The technology for collecting explosive particles in the disk-shaped filter and analyzing the explosive particles with the use of the analyzer needs two steps, i.e., a step of adsorption of the particles and a step of thermal vaporization, and therefore real-time analysis cannot be continuously performed. Further, the technology sequentially implements the adsorption step, the thermal vaporization step, and a cleaning step and returns to the adsorption step again by rotating the disk-shaped filter portion. Thus, the filter portion cannot be used as some evidence in future. It takes time to detach a filter as evidence each time while maintaining a configuration of the apparatus.

The technology disclosed in PTL 1 is premised on the assumption that a filter for collecting particles is used after the filter is heated to a higher temperature than a room temperature. Therefore, the apparatus cannot be used until the filter has an appropriate temperature after the filter is attached, and thus analysis cannot be continued without interrupting the apparatus for a long time.

From the above reasons, there is required an analyzing apparatus capable of analyzing particles instead of gas, continuously performing real-time analysis, and completing necessary filter replacement within a satisfactorily short time.

Solution to Problems

A particle analyzing apparatus of the invention includes: a concentration unit for concentrating gas containing particles to be detected; a thermal vaporization unit for collecting the particles in the gas concentrated in the concentration unit and thermally vaporizing the particles; and an analysis unit for analyzing a sample thermally vaporized in the thermal vaporization unit. The thermal vaporization unit includes a plurality of filters and has a mechanism which can replace a filter with the next filter when the filter is spent. Further, a filter which is currently used is heated and a filter to be used next by filter replacement is preheated.

That is, the thermal vaporization unit includes a flow channel connecting the concentration unit and the analysis unit, a first filter loaded into the flow channel, a seal portion for sealing the periphery of the flow channel in a state in which the first filter is loaded, a heating unit for heating the first filter, a second filter which is located outside the flow channel and is to be loaded into the flow channel and be used next, a preheating unit for heating the second filter, and a filter replacement mechanism for unloading the first filter from the flow channel and loading the second filter into the flow channel.

Advantageous Effects of Invention

According to the invention, it is possible to analyze particles, continuously perform real-time analysis, and complete necessary filter replacement within a satisfactorily short time.

Problems, configurations, and effects other than those described above will be disclosed by the description of embodiments described below.

DESCRIPTION OF EMBODIMENTS

Hereinafter, embodiments of the invention will be described with reference to drawings.

Figure 1:
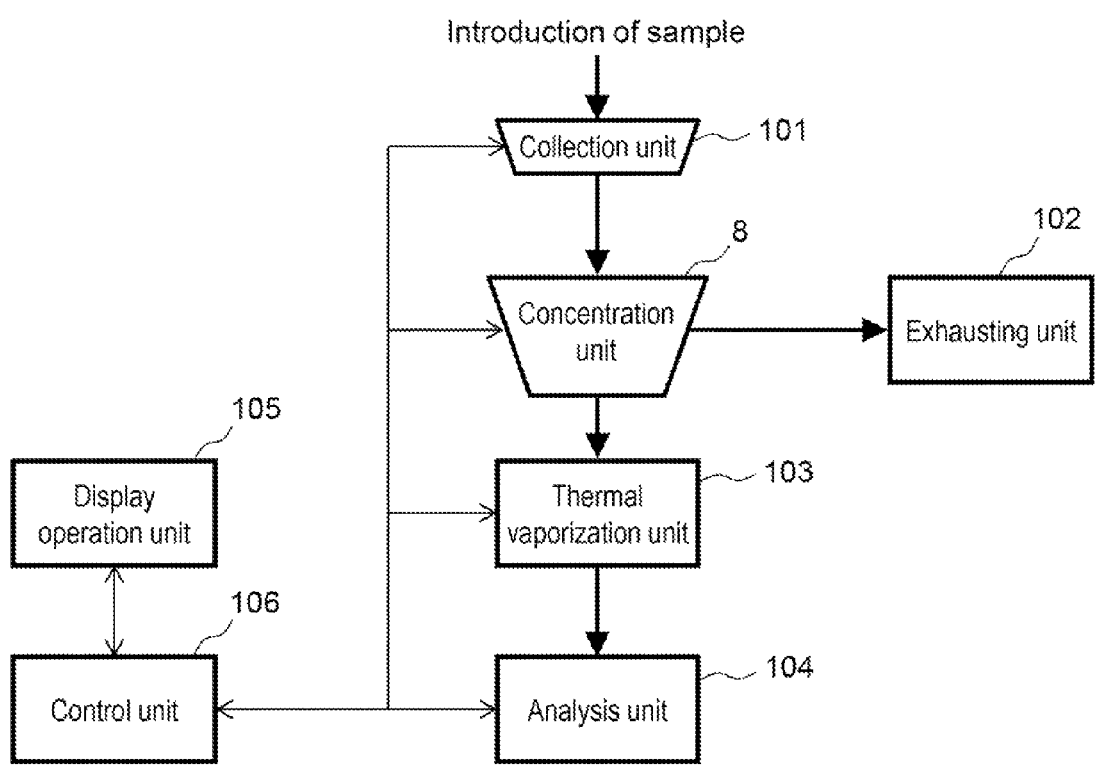
FIG. 1 is a system configuration diagram of an example of a particle analyzing apparatus.
Figure 2:
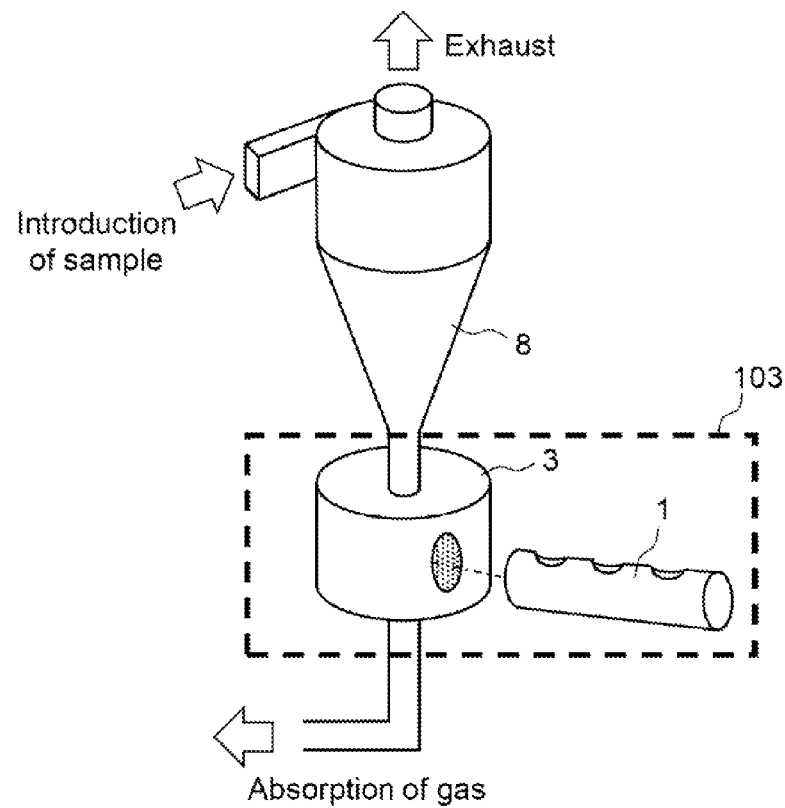
FIG. 2 is a schematic diagram of a configuration example of the particle analyzing apparatus.

An entire configuration of a particle analyzing apparatus according to the invention will be described. FIG. 1 is a system configuration diagram of an example of a particle analyzing apparatus. FIG. 2 is a schematic diagram of a configuration example of the particle analyzing apparatus.

As illustrated in FIG. 1, a sample which is gas containing particles to be analyzed is introduced through a collection portion 101 and is concentrated in a concentration unit 8. Unnecessary exhaust is discharged from an exhausting unit 102, and only the concentrated sample is sent to a thermal vaporization unit 103. The sample that has been thermally vaporized in the thermal vaporization unit 103 is sent to an analysis unit 104, and an analysis result is transmitted to a display operation unit 105 via a control unit 106.

In FIG. 2, a sample which is gas containing particles is supplied to the concentration unit 8 through a sample introduction port. Unnecessary gas is exhausted from an upper portion, and residual gas containing a high percentage of the particles is caused to flow into a filter cartridge 1 which is loaded and provided in a filter holder 3. In this example, the thermal vaporization unit 103 includes the filter cartridge 1 and the filter holder 3. A filter is incorporated in the filter cartridge 1 as described below, and the filter is heated together with the filter cartridge 1 by a heater incorporated in the filter holder 3. The gas supplied from the concentration unit 8 to the filter holder 3 passes through an opening portion of the filter holder, further passes through the filter, and is then sucked through a lower portion. At this time, the particles contained in the gas are collected by the filter held by the filter cartridge 1, are heated and gasified therein, and are sucked through the lower portion in the same way as the gas. The sucked gas is introduced into the analysis unit and components thereof are analyzed.

The filter can be made of, for example, a stainless steel mesh material having filtration accuracy of about 0.3 µm to 1.0 µm. Herein, the filter may collect various foreign substances other than particles to be analyzed, such as dust floating in the air. In the case where a large amount of foreign substances are accumulated on the filter due to long analysis work, for example, noise components generated from the foreign substances are gradually increased, resulting in obstruction of analysis. In addition, for example, gas passing efficiency of the filter is reduced and thermal conductivity to a surface portion of the filter is reduced, resulting in reduction of efficiency of the entire apparatus. Thus, in the case where foreign substances and the like are accumulated on the filter, the filter needs to be replaced.

Figure 3:
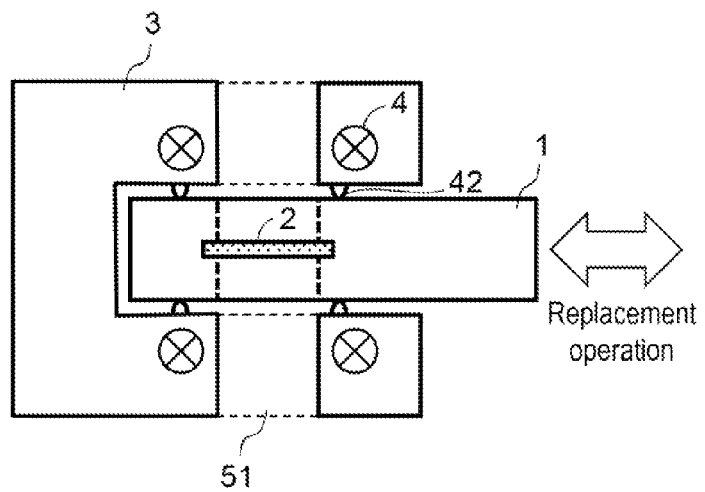
FIG. 3 is a cross-sectional schematic diagram of a configuration example of a conventional filter holder and a conventional filter cartridge.

FIG. 3 is a cross-sectional schematic diagram of a configuration example of a conventional filter holder and a conventional filter cartridge. A filter 2 is fixedly incorporated in the filter cartridge 1 and is replaced together with the filter cartridge 1. That is, in the case of filter replacement, as indicated by an arrow in FIG. 3, the filter cartridge 1 is removed from the filter holder 3, and a new filter cartridge 1 is loaded. Seal portions 42 are provided by metal touch between the filter holder 3 and the filter cartridge 1, and a flow channel of gas is formed via a filter holder opening portion 51 by appropriately loading the filter cartridge 1 into the filter holder 3.

In such a configuration, the filter cartridge 1 needs to be reciprocated for replacement, and therefore continuous replacement is difficult. Further, because particles cannot be gasified until heating of the newly loaded filter cartridge 1 to increase a temperature thereof is completed by a heater 4, it is difficult to reduce a downtime of the apparatus caused by filter replacement.

The invention can easily replace a filter without interrupting analysis in the particle analyzing apparatus having a general configuration illustrated in FIG. 1 and FIG. 2. Hereinafter, a configuration of a part regarding filter replacement in the configuration of the particle analyzing apparatus will be described in detail.

(A) Embodiment 1

Figure 4:
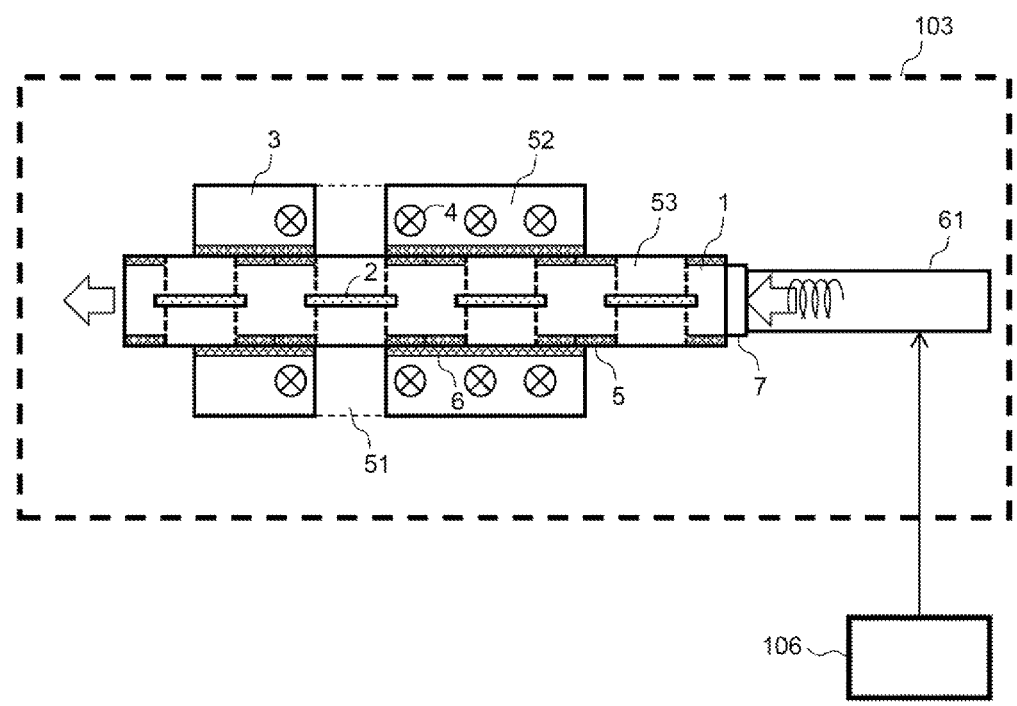
FIG. 4 is a cross-sectional schematic diagram of a configuration example of a thermal vaporization unit of a particle analyzing apparatus according to the invention.

FIG. 4 illustrates Embodiment 1 of the invention and is a cross-sectional schematic diagram of a thermal vaporization unit 103 of a particle analyzing apparatus according to this embodiment. Note that a system configuration of the particle analyzing apparatus is illustrated in FIG. 1 and an entire configuration of the apparatus is illustrated in FIG. 2.

In FIG. 4, 1 is a replaceable filter cartridge, 2 is a filter held by the filter cartridge, 3 is a filter holder incorporated in the particle analyzing apparatus, 4 is a heater, 5 is a male screw seal portion included in the filter cartridge, 6 is a female screw seal portion included in the filter holder, 7 is a bolt head portion, 51 is a filter holder opening portion, 52 is a preheating unit, 61 is a sending unit, and 106 is a control unit.

Hereinafter, operation of this embodiment will be described. The plurality of filters 2 are incorporated in the filter cartridge 1. An outer shape of the filter cartridge 1 is a substantially columnar shape, and a male screw is provided in an outer circumference thereof. In a part where each filter 2 is held in the filter cartridge 1, a flow channel formation through hole 53 crossing the filter cartridge and extending in a direction perpendicular to a surface of the filter 2 is provided. The filter 2 is provided to block the flow channel formation through hole 53. When the flow channel formation through hole 53 of the filter cartridge 1 and the filter holder opening portion 51 are arranged in a line, a flow channel connecting a concentration unit 8 and an analysis unit 104 via the filter 2 is formed, and the particle analyzing apparatus is used in a state in which the flow channel is formed.

The filter holder 3 includes the heater 4 and has a substantially cylindrical hole having an inner circumference in which a female screw is provided. The male screw of the filter cartridge 1 is fitted to the female screw of the filter holder 3. With this, the filter cartridge 1 can move forward while turning in the filter holder 3. Turning operation of the filter cartridge 1 is performed by applying a turning force to the bolt head portion 7 provided in a rearmost end of the filter cartridge 1 from the sending unit 61 under control of the control unit 106. Further, by fitting a male screw portion of the filter cartridge 1, i.e., the male screw seal portion 5, and a female screw portion of the filter holder 3, i.e., the female screw seal portion 6 to each other, a gap between the filter cartridge 1 and the filter holder 3 is substantially sealed. A seal portion including the male screw seal portion 5 and the female screw seal portion 6 seals the periphery of the flow channel connecting the concentration unit 8 and the analysis unit 104, the flow channel being formed by arranging the flow channel formation through hole 53 of the filter cartridge 1 and the filter holder opening portion 51 of the filter holder 3 in a line.

In the case where the filter 2 is replaced, a turning force is applied to the bolt head 7 from the sending unit 61, thereby turning the filter cartridge, i.e., moving the filter cartridge 1 forward, and the filter cartridge is turned a predetermined number of times, thereby positioning a new unused filter with respect to the filter holder opening portion 51. A filter heating unit includes the heater 4 located in the periphery of the filter holder opening portion 51, and the filter 2 provided in the filter holder opening portion 51 is heated by thermal conduction via the filter cartridge 1 from the filter holder 3 heated by the filter heating unit. Herein, the filter 2 is heated within a range of 200° C. to 250° C. This is because, in this embodiment, particles to be detected, which is to be collected and gasified in the filter 2, are explosive particles and a boiling point of a typical substance (e.g., RDX) thereof falls within the above temperature range.

Meanwhile, a used filter 2 is gradually pushed out of the filter holder 3 in accordance with forward movement of the filter cartridge 1 and is unloaded from a left side of FIG. 4.

The cylindrical hole of the filter holder 3 in which the female screw seal portion 6 is provided has an enough length to cover two or more filters 2 incorporated in the filter cartridge 1 and is extended in a direction from the filter holder opening portion 51 to a loading port of the filter cartridge 1. A part of the filter holder 3, which is extended toward the loading port of the filter cartridge, is the preheating unit 52, and the heater 4 is included not only in the periphery of the filter holder opening portion 51 but also in the preheating unit 52. With this, a replacement filter to be used next, as well as a filter which is currently used, is heated when the replacement filter is located in the preheating unit 52 before being positioned in the filter holder opening portion 51.

As described above, instead of heating the filter 2 positioned in the filter holder opening portion 51 after the filter cartridge 1 is operated to move forward, an unused filter 2 is heated in advance in the preheating unit 52. Therefore, a filter heating time in the filter holder opening portion 51 as preparation before use can be extremely reduced or can be reduced to zero.

Herein, constant preheating is assumed, and a replacement filter to be used next, which is located in the preheating unit 52, is preheated for a time period equal to a time period in which a filter which is located and currently used in the filter holder opening portion 51 is heated. In this embodiment, the heating unit in the periphery of the filter holder opening portion 51 and the preheating unit 52 are integrally formed as a continuous structure by a material having high thermal conductivity such as metal. With this, the heating unit in the periphery of the filter holder opening portion 51 and the preheating unit 52 have substantially the same temperature. Note that, because the filter holder 3 and the filter cartridge 1 need to be heated to a higher temperature than a room temperature in a state in which those are fitted to each other, the filter holder 3 and the filter cartridge 1 are preferably formed by materials having substantially the same coefficient of linear expansion.

Figure 5:
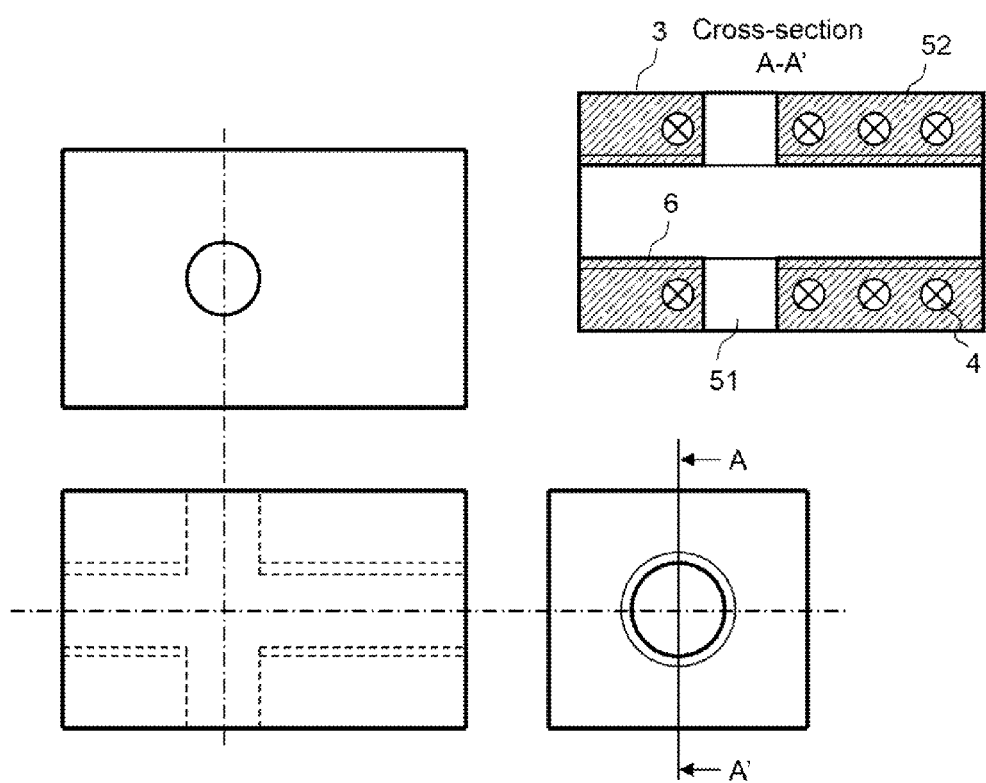
FIG. 5 is a schematic structure example of a filter holder.
Figure 6:
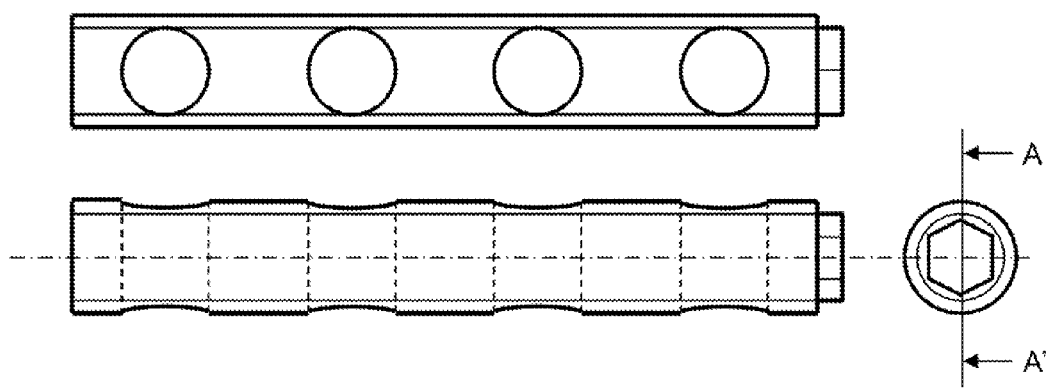
FIG. 6 is a schematic structure example of a filter cartridge.
Figure 6:
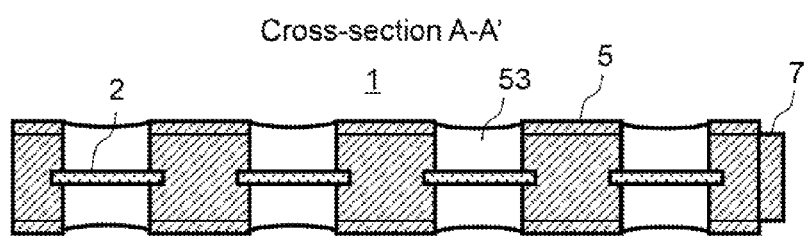

Structures of the filter holder and the filter cartridge will be described with reference to FIG. 5 and FIG. 6. FIG. 5 is mechanical drawings (based on third angle projection) illustrating a schematic structure of the filter holder 3. FIG. 6 is mechanical drawings (based on third angle projection) illustrating a schematic structure of the filter cartridge 1. In each of FIGS. 5 and 6, a cross-sectional view taken along a cutting position A-A' is also illustrated.

Figure 7:
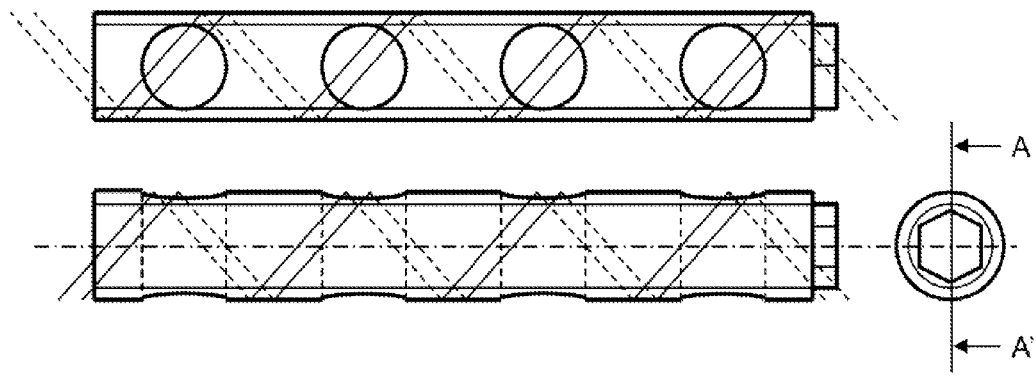
FIG. 7 is a schematic structure example of the filter cartridge.
Figure 7:
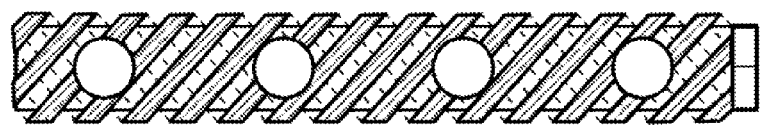

FIG. 7 illustrates a schematic structure of the filter cartridge 1 in this embodiment, seen from another point of view. FIG. 7 illustrates an example of a shape of the male screw formed in the outer circumference of a columnar surface of the filter cartridge 1 and is a top conceptual diagram, a side conceptual diagram, and an external view from the top. FIG. 7 illustrates an example of a four-start thread in which a lead of the screw is four times as much as a pitch. With this screw shape, the filter cartridge 1 moves forward by a length of a single opening portion each time when the filter cartridge 1 is turned once and moves forward by a length of a half the opening portion each time when the filter cartridge 1 is turned half a turn. That is, in a state in which the filter cartridge 1 is vertically inverted, the flow channel formation through hole 53 of the filter cartridge 1 is not positioned to correspond to the opening portion of the filter holder 3.

With this configuration, it is possible to securely prevent foreign substances which have been collected on an upper surface of the filter 2 but have not been gasified yet from falling toward the analysis unit through the hole which is open in a lower portion of the filter holder 3.

Note that, needless to say, the female screw of the filter holder 3 needs to be formed by the same specification as that of the male screw of the filter cartridge 1. Herein, although the four-start thread has been described, any single-start or multi-start thread may be employed as long as a length of the lead of the screw equals to that of a single opening portion of the filter cartridge 1.

As described above, the flow channel connecting the concentration unit and the analysis unit is provided in the thermal vaporization unit of the particle analyzing apparatus, and the thermal vaporization unit includes a first filter loaded into the flow channel, the seal portion for sealing the periphery of the flow channel in a state in which the first filter is loaded, the heating unit for heating the first filter, a second filter which is located outside the flow channel and is to be loaded next into the flow channel, the preheating unit for heating the second filter, and a filter replacement mechanism for unloading the first filter from the flow channel and loading the second filter into the flow channel. Thus, it is possible to analyze particles, extremely reduce the filter heating time as preparation before use or reduce the filter heating time to zero, thereby continuously performing real-time analysis, and complete necessary filter replacement within a satisfactorily short time.

The first filter is heated by the heating unit within a range of 200° C. to 250° C. Thus, it is possible to thermally vaporize explosive particles collected in the filter and analyze the explosive particles.

Filter replacement is performed by incorporating the first filter and the second filter in the filter cartridge and driving the filter cartridge by using the filter replacement mechanism to move the first filter and the second filter in a direction crossing the flow channel. Thus, it is possible to complete the filter replacement within a satisfactorily short time.

The filter cartridge has the columnar shape and has the outer circumference in which the male screw is formed. The filter holder has a cylindrical hole and has the inner circumference in which the female screw is formed to be fitted to the male screw. The filter replacement mechanism is a mechanism for loading the male screw into the female screw to perform rotation and forward movement. Sealing is performed by engagement of the male screw with the female screw. Thus, by causing the filter replacement mechanism to also function as the seal portion, it is possible to securely perform sealing.

At this time, a lead length of the male screw formed in the outer circumference of the filter cartridge and a lead length of the female screw formed in the inner surface of the filter holder are set to be equal to a pitch distance of the plurality of filters held by the filter holder. Thus, it is possible to securely prevent foreign substances collected on the upper surface of the filter from falling toward the analysis unit through the opening portion of the filter holder.

The heating unit and the preheating unit are integrally included in the filter holder and simultaneously heat the first filter and the second filter. Thus, the heating unit and the preheating unit can be set to have substantially the same temperature, and the filter heating time as preparation before use can be extremely reduced or can be reduced to zero, thereby continuously performing real-time analysis.

(B) Embodiment 2

Figure 8:
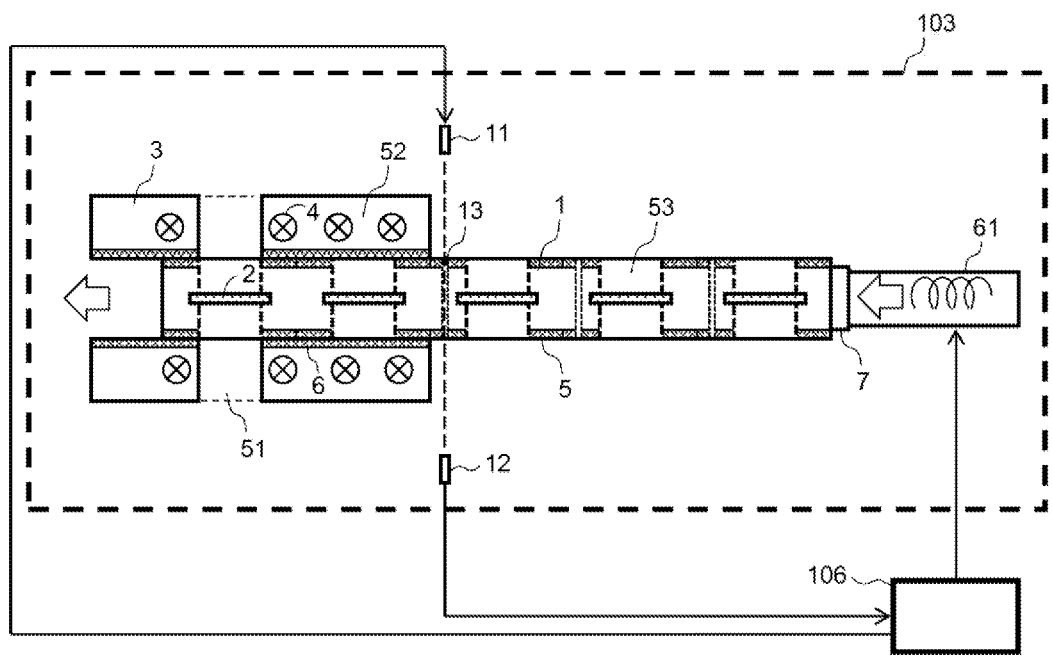
FIG. 8 is a cross-sectional schematic diagram of a configuration example of a thermal vaporization unit of a particle analyzing apparatus according to the invention.

FIG. 8 illustrates Embodiment 2 of the invention and is a cross-sectional schematic diagram of a thermal vaporization unit 103 of a particle analyzing apparatus according to this embodiment.

In FIG. 8, 1 is a filter cartridge, 2 is a filter, 3 is a filter holder, 4 is a heater, 5 is a male screw seal portion, 6 is a female screw seal portion, 7 is a bolt head portion, 11 is a light source, 12 is a photodetector, 13 is a detection hole, 51 is a filter holder opening portion, 52 is a preheating unit, 61 is a sending unit, and 106 is a control unit.

Hereinafter, operation of this embodiment will be described. Because a configuration and the operation of Embodiment 2 are similar to those of Embodiment 1, a different between both embodiments will be mainly described herein.

In Embodiment 2, the plurality of detection holes 13 are provided in the filter cartridge 1. The particle analyzing apparatus includes the light source 11 and the photodetector 12. The light source 11 emits light beams such as laser light beams toward the photodetector 12, and an optical path connecting the light source 11 and the photodetector 12 is set to intersect with a path through which the filter cartridge 1 moves forward. The light beams emitted from the light source 11 and passing through the detection hole 13 are detected by the photodetector 12. Those additional configuration elements are provided to accurately position the filter cartridge 1.

In Embodiment 1, positioning of the filter cartridge 1 is controlled by an amount of turning of the bolt head portion 7. Meanwhile, in Embodiment 2, how far the filter cartridge moves forward is controlled more accurately by detecting that the detection hole 13 of the filter cartridge 1 is arranged between the light source 11 and the photodetector 12. That is, the control unit 106 controls turning operation of the filter cartridge 1 by the sending unit 61 while monitoring an output signal of the photodetector 12. When light beams emitted from the light source 11 pass through the detection hole 13 of the filter cartridge 1 and are detected by the photodetector 12, the control unit 106 instructs, in response to a signal of the photodetector 12, the sending unit 61 to stop the turning operation of the filter cartridge 1. This makes it possible to perform positioning of the filter cartridge 1 with high accuracy.

Herein, the detection hole 13 is preferably positioned apart as far as possible from the filter 2 incorporated in the filter cartridge 1. This makes it possible to maintain a sealing effect between the filter cartridge 1 and the filter holder 3, the sealing effect being obtained by the male screw seal portion 5 and the female screw seal portion 6. In the example of FIG. 8, the detection hole 13 is provided to penetrate the filter cartridge 1 through a central axis thereof in the same direction as that of the flow channel formation through hole 53 of the filter cartridge 1. However, a direction and an arrangement position of the detection hole 13 are not limited thereto, and the detection hole 13 may be provided in a direction orthogonal thereto and may be provided to pass through a position offset from the central axis of the filter cartridge 1.

The detection hole 13 does not even need to be a hole and may be a cutout provided in an outer circumferential portion of the male screw seal portion 5. In this case, as a matter of course, the light source 11 and the photodetector 12 need to be arranged so that the light beam from the light source 11 to the photodetector 12 does not pass through the central axis of the filter cartridge 1 but through the outer circumferential portion of the filter cartridge 1.

Figure 9:
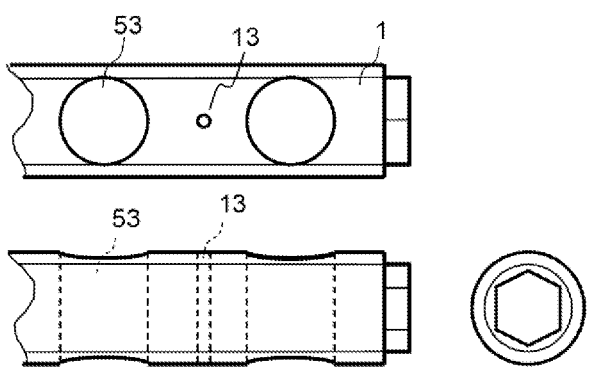
FIG. 9 illustrates an example of a detection hole provided in a filter cartridge.
Figure 10:
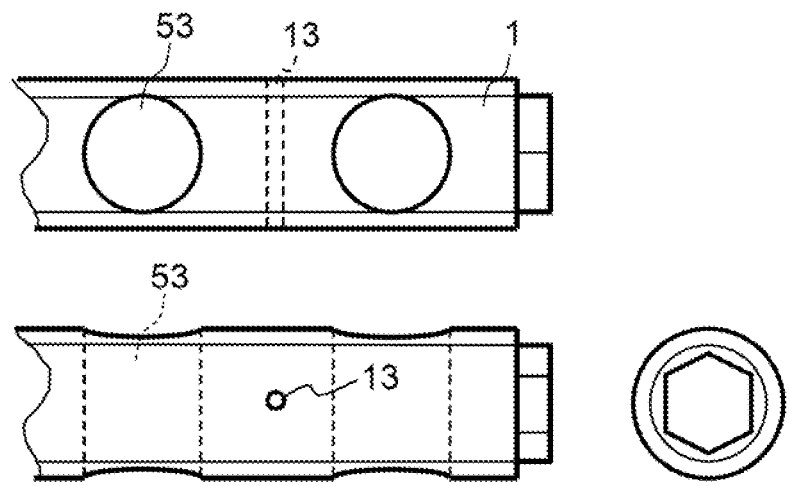
FIG. 10 illustrates an example of a detection hole provided in the filter cartridge.
Figure 11:
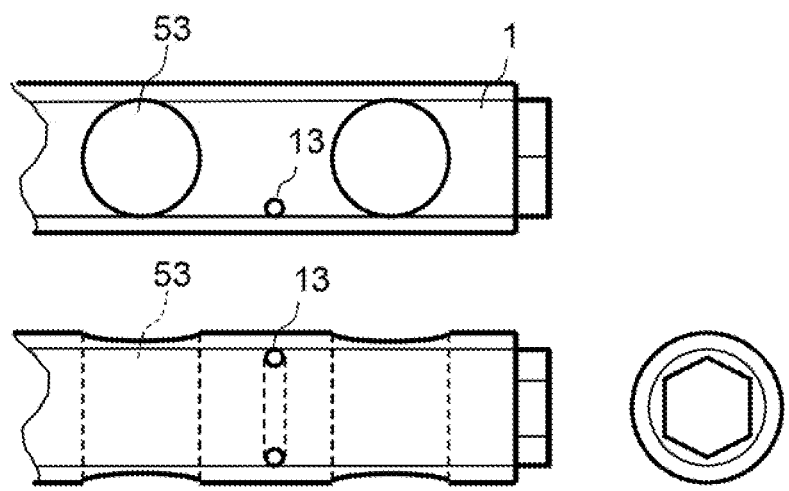
FIG. 11 illustrates an example of a detection hole provided in the filter cartridge.
Figure 12:
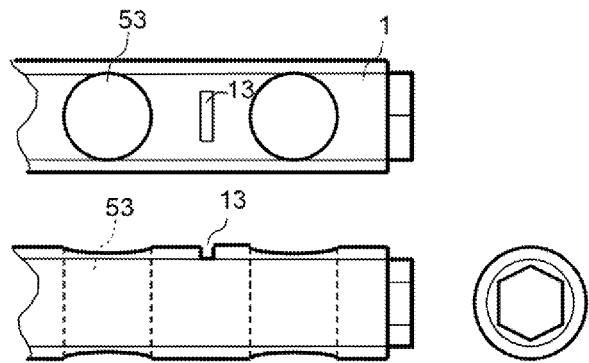
FIG. 12 illustrates an example of a detection hole provided in the filter cartridge.

In order to assist understanding of this embodiment, examples of a schematic structure of the detection hole 13 provided in the filter cartridge 1 are illustrated in FIGS. 9 to 12. FIG. 9 illustrates an example where the detection hole 13 is extended in the same direction as an axis of the flow channel formation through hole 53 provided in the filter cartridge 1, i.e., in a direction orthogonal to a surface of the filter, and passes through the central axis of the filter cartridge 1. FIG. 10 illustrates an example where the detection hole 13 is extended in a direction orthogonal to the axis of the flow channel formation through hole 53, i.e., in a direction in parallel to the surface of the filter, and passes through the central axis of the filter cartridge 1. FIG. 11 illustrates an example where the detection hole 13 is extended in the same direction as the axis of the flow channel formation through hole 53, i.e., in the direction orthogonal to the surface of the filter, and passes through a position offset from the center of the filter cartridge 1. FIG. 12 illustrates an example where the detection hole 13 is formed as a cutout instead of a hole so as to be extended in the direction orthogonal to the axis of the flow channel formation through hole 53, i.e., in the direction in parallel to the surface of the filter. Thus, by providing the detection hole 13 at a position shifted from the center of rotation of the filter cartridge 1, uniqueness of the position can be improved.

As described above, the detection hole for position detection is provided in the filter cartridge, and the light source and the photodetector are provided in the filter replacement mechanism, and the filter replacement mechanism stops driving of the filter cartridge when light beams emitted from the light source pass through the detection hole of the filter cartridge and are detected by the photodetector. Thus, it is possible to improve positioning accuracy of the filter cartridge at the time of filter replacement.

Further, as described above, the cutout portion for position detection is provided in the filter cartridge, and the light source and the photodetector are provided in the filter replacement mechanism, and the filter replacement mechanism stops driving of the filter cartridge when light beams emitted from the light source pass through the cutout portion of the filter cartridge and are detected by the photodetector. Thus, it is possible to improve positioning accuracy of the filter cartridge at the time of filter replacement.

(C) Embodiment 3

Figure 13:
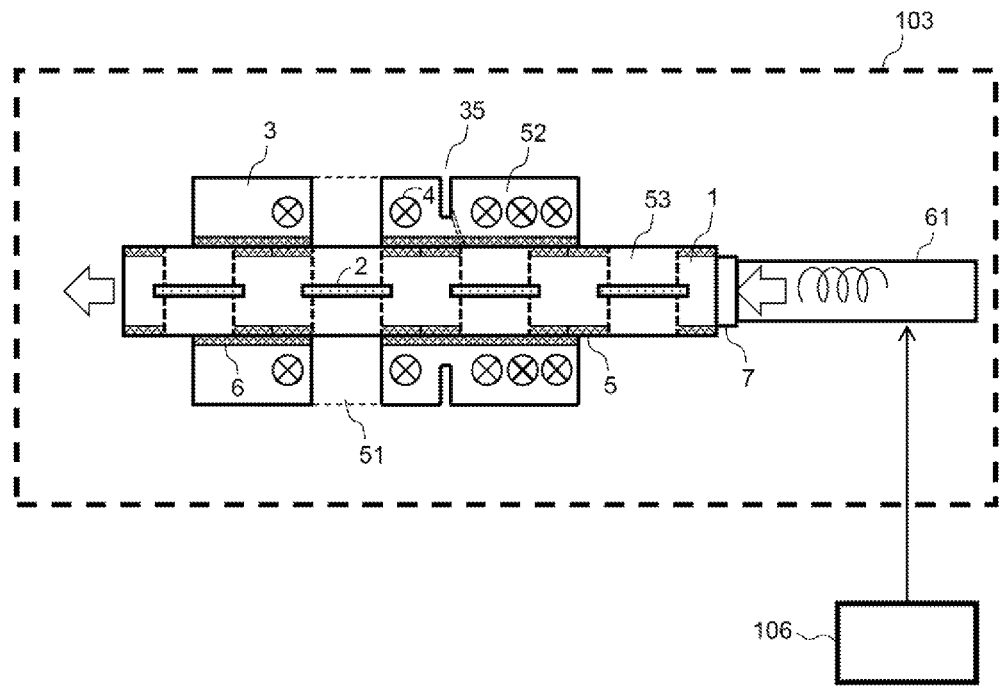
FIG. 13 is a cross-sectional schematic diagram of a configuration example of a thermal vaporization unit of a particle analyzing apparatus according to the invention.

FIG. 13 illustrates Embodiment 3 of the invention and is a cross-sectional schematic diagram of a thermal vaporization unit 103 of a particle analyzing apparatus according to this embodiment.

In FIG. 13, 1 is a filter cartridge, 2 is a filter, 3 is a filter holder, 4 is a heater, 5 is a male screw seal portion, 6 is a female screw seal portion, 7 is a bolt head portion, 51 is a filter holder opening portion, 52 is a preheating unit, 61 is a sending unit, and 106 is a control unit.

Hereinafter, operation of Embodiment 3 of the invention will be described. Because a configuration and the operation of Embodiment 3 are similar to those of Embodiment 1, a different between both embodiments will be mainly described herein.

In Embodiment 3, a cutout 35 is provided in the periphery of the filter holder 3, and a thermal resistance between the filter holder opening portion 51 and the preheating unit 52 is increased by the cutout 35. The preheating unit 52 includes the heaters 4 with a higher density than that of the heaters in the filter holder opening portion 51 so as to have a higher temperature.

In Embodiment 3, because the filter 2 is in a relatively high temperature environment while staying in the preheating unit 52, the filter 2 is preliminarily heated, and, in addition, foreign substances adhered to a surface of the filter 2 are thermally decomposed and removed. The foreign substances that have been thermally decomposed are discharged from a degassing hole provided in the vicinity of the preheating unit 52. With this configuration, dealing means of the filter cartridge 1 before the filter cartridge is loaded into the filter holder 3 can be set to a lower cleanliness level, and a configuration of the entire apparatus can be simplified.

The relatively high temperature only needs to be, for example, about 260° C. when a normal heating temperature is 250° C. This makes it possible to prevent other foreign substances, which are vaporized at a temperature substantially the same as a temperature of vaporization of substances to be detected (e.g., explosive particles), from being introduced into an analysis unit as a noise.

Note that, in this embodiment, the example where the heaters 4 are included with a high density has been described as means for causing the preheating unit 52 to have a relatively high temperature. However, the means for causing the preheating unit 52 to have a high temperature is not limited thereto, and heating properties of the heaters 4 of the filter holder opening portion 51 and the preheating unit 52 may differ.

The example where the cutout is provided between the filter holder opening portion 51 and the preheating unit 52 has been described as means for increasing the thermal resistance therebetween. Also in this case, the means is not limited thereto, and, for example, a material having a large thermal resistance may be interposed therebetween.

As described above, because the preheating unit is independent from the heating unit and the heating temperature by the preheating unit is set to be higher than the heating temperature by the heating unit, it is possible to thermally decompose and remove foreign substances adhered to the surface of the filter located in the preheating unit and prevent the foreign substances from being introduced into the analysis unit as a noise. Thus, the dealing means of the filter cartridge before the filter cartridge is loaded into the filter holder can be set to a lower cleanliness level, and the configuration of the entire apparatus can be simplified.

(D) Embodiment 4

Figure 14:
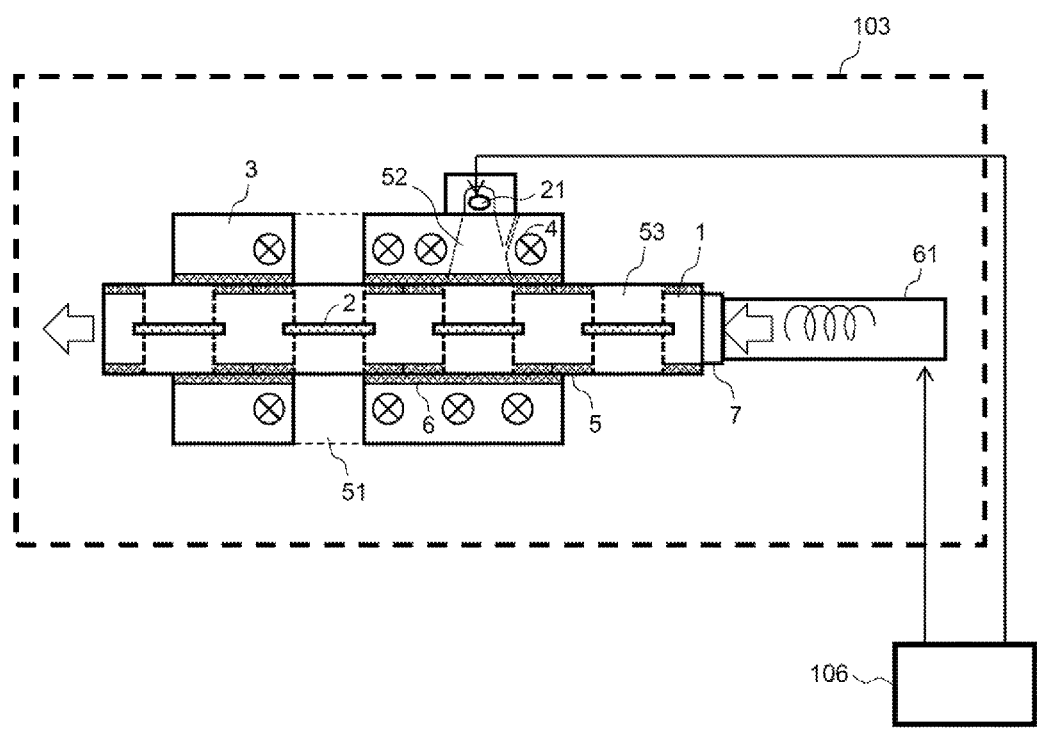
FIG. 14 is a cross-sectional schematic diagram of a configuration example of a thermal vaporization unit of a particle analyzing apparatus according to the invention.

FIG. 14 illustrates Embodiment 4 of the invention and is a cross-sectional schematic diagram of a thermal vaporization unit 103 of a particle analyzing apparatus according to this embodiment.

In FIG. 14, 1 is a filter cartridge, 2 is a filter, 3 is a filter holder, 4 is a heater, 5 is a male screw seal portion, 6 is a female screw seal portion, 7 is a bolt head portion, 21 is a halogen lamp heater, 51 is a filter holder opening portion, 52 is a preheating unit, 61 is a sending unit, and 106 is a control unit.

Hereinafter, operation of Embodiment 4 of the invention will be described. Because a configuration and the operation of Embodiment 4 are similar to those of Embodiment 3, a different between both embodiments will be mainly described herein.

In Embodiment 4, the halogen lamp heater 21 is included in the preheating unit 52. The filter 2 located in the preheating unit 52 is preliminarily heated by the heater 4. In addition to this, in this embodiment, in order to thermally decompose and remove foreign substances adhered to a surface of the filter 2, additional heating is performed by the halogen lamp heater 21. The additional heating to thermally decompose foreign substances needs to be performed only for a relatively short time, and it is not always necessary to maintain the foreign substances in this environment for a long time. Thus, instead of the configuration in which the heaters 4 are included with a high density, heating means capable of heating a target object within a short time by infrared radiation, such as the halogen lamp heater 21, is provided to thermally decompose foreign substances. Gas containing the foreign substances that have been thermally decomposed is discharged from a degassing hole provided in the vicinity of the additional heating means. Herein, the short time is, for example, about several tens of seconds. A timing at which additional heating is performed is desirably after a new filter is introduced into the preheating unit 52 and reaches a preheating target temperature but before the new filter is sent to the filter holder opening portion 51. For example, the following operation timing can be employed: additional heating is performed several tens of seconds before a filter is sent to the next position, and the filter is sent when the additional heating for several tens of seconds is completed.

Note that the means is not limited to the halogen lamp heater as long as the means can perform heating within a short time, and heating may be performed by using similar means as appropriate.

As described above, because the infrared radiation means is included in the preheating unit, foreign substances adhered to the surface of the filter can be thermally decomposed by additional heating for a short time.

(E) Embodiment 5

Figure 15:
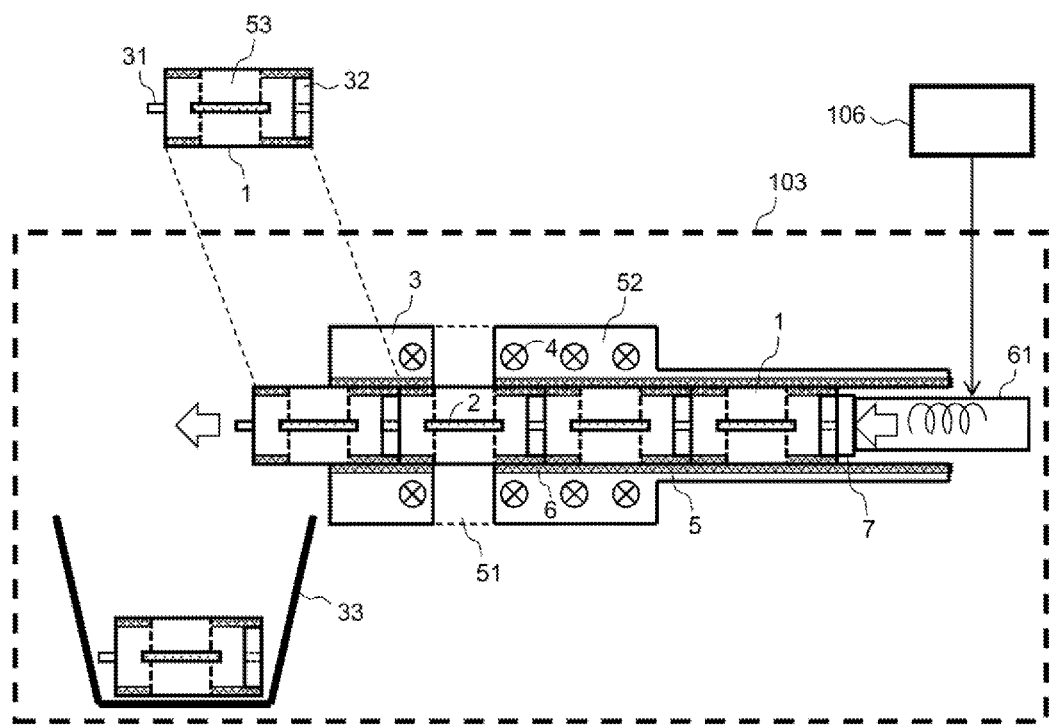
FIG. 15 is a cross-sectional schematic diagram of a configuration example of a thermal vaporization unit of a particle analyzing apparatus according to the invention.

FIG. 15 illustrates Embodiment 5 of the invention and is a cross-sectional schematic diagram of a thermal vaporization unit 103 of a particle analyzing apparatus according to this embodiment.

In FIG. 15, 1 is a filter cartridge, 2 is a filter, 3 is a filter holder, 4 is a heater, 5 is a male screw seal portion, 6 is a female screw seal portion, 7 is a bolt head portion, 31 is a front surface fitting portion, 32 is a back surface fitting portion, 33 is a cartridge collection portion, 51 is a filter holder opening portion, 52 is a preheating unit, 61 is a sending unit, and 106 is a control unit.

Hereinafter, operation of Embodiment 5 of the invention will be described. Because a configuration and the operation of Embodiment 5 are similar to those of Embodiment 1, a different between both embodiments will be mainly described herein.

In Embodiment 5, the plurality of filter cartridges 1 are connected in an axial direction thereof. A single filter cartridge 1 includes a single filter 2, and each filter cartridge has the front surface fitting portion 31 in a front surface thereof and has the back surface fitting portion 32 in a back surface thereof. The plurality of filter cartridges are connected by fitting a front surface fitting portion 31 of a single filter cartridge 1 to a back surface fitting portion 32 of another filter cartridge 1 which is located immediately ahead of the single filter cartridge 1. The plurality of filter cartridges 1 are loaded into the filter holder 3 in a state in which the filter cartridges 1 are connected to each other and move forward while turning in the same way as Embodiment 1. As to a used filter cartridge 1, connection of the filter cartridges is released after the filter cartridge 1 is completely removed from the filter holder 3, and the filter cartridge 1 is collected in the cartridge collection portion 33.

With this configuration, in the case where filter replacement is frequent in particular, it is easy to secure a space for receiving the used filter cartridge 1. Further, it is also easy to secure a space for receiving an unused filter cartridge 1.

Note that, herein, the example where a single filter 2 is incorporated in a single filter cartridge 1 has been described. However, as a matter of course, the invention is not limited to this configuration, and two or more filters 2 may be incorporated in a single filter cartridge.

As described above, because the plurality of filter cartridges, each of which includes one or two or more filters, are connected in the axial direction and are loaded into the filter holder, space saving can be achieved.

(F) Embodiment 6

Figure 16:
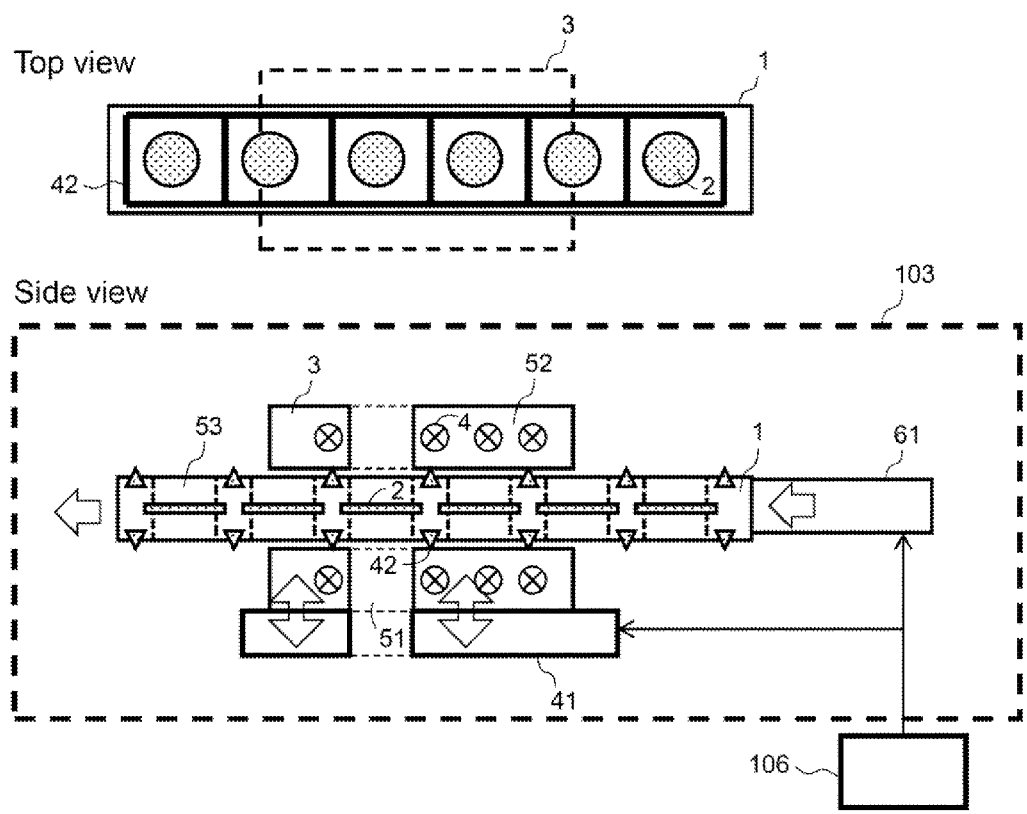
FIG. 16 is a cross-sectional schematic diagram of a configuration example of a thermal vaporization unit of a particle analyzing apparatus according to the invention.

FIG. 16 illustrates Embodiment 6 of the invention and is a cross-sectional schematic diagram of a thermal vaporization unit 103 of a particle analyzing apparatus according to this embodiment.

In FIG. 16, 1 is a filter cartridge, 2 is a filter, 3 is a filter holder, 4 is a heater, 41 is a vertical motion sandwiching mechanism, 42 is a seal portion, 51 is a filter holder opening portion, 52 is a preheating unit, 61 is a sending unit, and 106 is a control unit.

Hereinafter, operation of Embodiment 6 of the invention will be described. In Embodiment 6, as means for performing sealing between the filter cartridge 1 and the filter holder 3, a mechanism for sandwiching the seal portions 42 from above and below is employed instead of the screw mechanism in the above embodiments. The seal portions 42 are provided in upper and lower surfaces of the filter cartridge 1 so as to surround the individual filters 2. The vertical motion sandwiching mechanism 41 is operated to sandwich the filter cartridge 1 from above and below with the use of a filter cartridge facing surface of the filter holder 3, thereby pressing and deforming the seal portions 42. Therefore, at least the periphery of the filter holder opening portion 51 is sealed.

For ease of description, herein, the filter cartridge 1 is assumed to have a rectangular parallelepiped outer shape. That is, the upper surface and the lower surface of the filter cartridge 1 are assumed to be plane surfaces, and surfaces of the filter holder 3, which face the upper surface and the lower surface, are also assumed to be plane surfaces. The seal portions 42 are provided therebetween, and, when the filter holder 3 sandwiches the filter cartridge 1 by using the vertical motion sandwiching mechanism, sealing is performed by a function of the seal portions 42. When filter replacement is performed, the control unit 106 loosens the vertical motion sandwiching mechanism 41 to release the filter cartridge 1 from the filter holder 3, causes the sending unit 61 to move the filter cartridge 1 forward until the next filter 2 is positioned in the filter holder opening portion 51, and causes the vertical motion sandwiching mechanism 41 to sandwich the filter cartridge 1 again.

Note that, in this embodiment, the example where the seal portions 42 are included in the filter cartridge 1 has been described. However, the invention is not limited thereto, and the seal portions 42 may be included in the filter holder 3. Further, the filter cartridge 1 does not always need to have a rectangular parallelepiped shape, and the surfaces of the filter cartridge 1 and the filter holder 3 which face each other do not always need to be plane surfaces. It is only necessary that the filter cartridge 1 and the filter holder 3 are shaped to be sealed without any gap.

As described above, the filter holder has a driving mechanism for performing operation for sandwiching the filter cartridge, and the seal portion performs sealing by bringing the filter holder into contact with the filter cartridge by the sandwiching operation of the driving mechanism. This makes it possible to securely perform sealing and satisfactorily perform heat transmission between the heating unit and the filter cartridge.

(G) Embodiment 7

Figure 17:
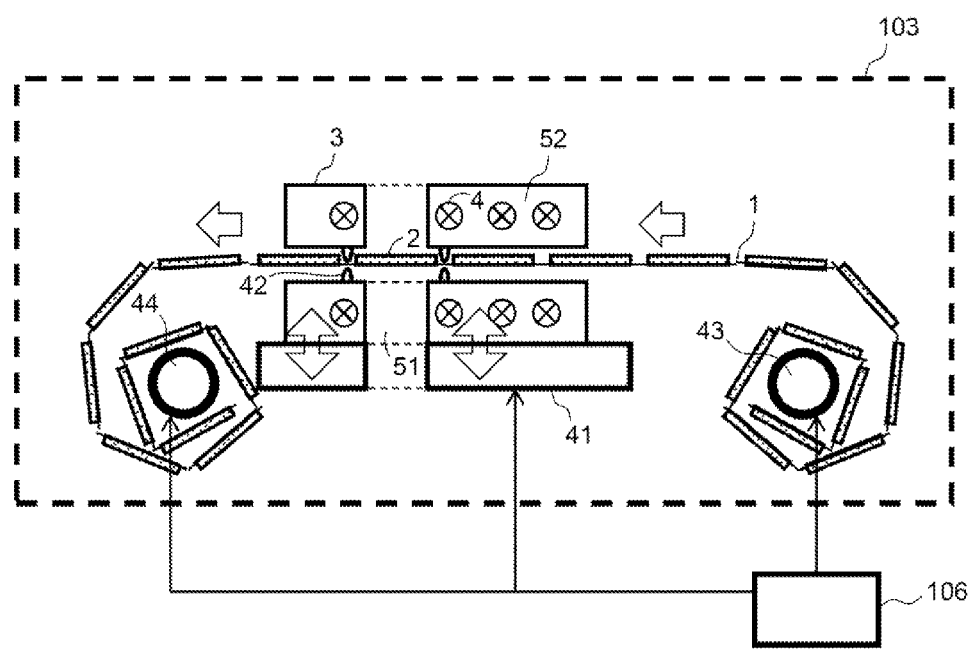
FIG. 17 is a cross-sectional schematic diagram of a configuration example of a thermal vaporization unit of a particle analyzing apparatus according to the invention.

FIG. 17 illustrates Embodiment 7 of the invention and is a cross-sectional schematic diagram of a thermal vaporization unit 103 of a particle analyzing apparatus according to this embodiment.

In FIG. 17, 1 is a filter cartridge, 2 is a filter, 3 is a filter holder, 4 is a heater, 41 is a vertical motion sandwiching mechanism, 42 is a seal portion, 43 is a delivery mechanism unit, 44 is a winding mechanism unit, 51 is a filter holder opening portion, 52 is a preheating unit, and 106 is a control unit.

Hereinafter, operation of Embodiment 7 of the invention will be described. Because a configuration and the operation of Embodiment 7 are similar to those of Embodiment 6, a different between both embodiments will be mainly described herein.

In Embodiment 7, a form of the filter cartridge 1 is a windable sheet-like shape, which is different from a bar-shape in the above embodiments. The sheet-like filter cartridge 1 is wound around the delivery mechanism unit 43 at the start of use and is moved forward by winding the sheet-like filter cartridge 1 around the winding mechanism unit 44 each time when filter replacement operation is performed. At the time of filter replacement, the control unit 106 lowers the vertical motion sandwiching mechanism 41 to loosen the seal portion 42 and then operates the delivery mechanism unit 43 and the winding mechanism unit 44 to position the next unused filter 2 in the filter holder opening portion 51. Subsequently, the control unit 106 raises the vertical motion sandwiching mechanism 41 and sandwiches and seals the filter cartridge 1 by using the seal portion 42. Thus, the filter replacement is completed. In order to satisfactorily perform sealing, it is preferable that the plurality of filters 2 be provided in the filter cartridge 1 so as to have a gap between adjacent filters and, at the time of sealing, sealing be performed by inserting the seal portion 42 provided in the filter holder 3 into the gap.

Note that, in this embodiment, the filter 2 is illustrated to have an uncurved structure. However, the filter 2 does not always need to have such a structure and may be formed by a material which is freely curved.

As described above, because the form of the filter cartridge is the windable sheet-like shape, space saving and reduction in costs can be achieved.

(H) Embodiment 8

Figure 18:
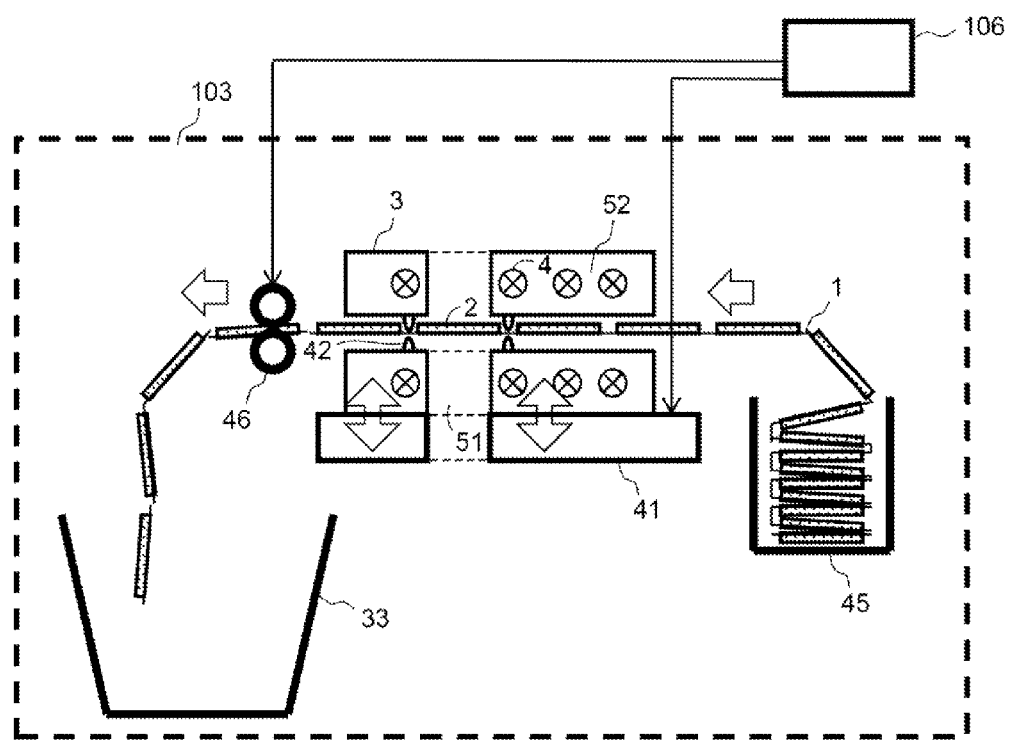
FIG. 18 is a cross-sectional schematic diagram of a configuration example of a thermal vaporization unit of a particle analyzing apparatus according to the invention.

FIG. 18 illustrates Embodiment 8 of the invention and is a cross-sectional schematic diagram of a thermal vaporization unit 103 of a particle analyzing apparatus according to this embodiment.

In FIG. 18, 1 is a filter cartridge, 2 is a filter, 3 is a filter holder, 4 is a heater, 33 is a cartridge collection portion, 41 is a vertical motion sandwiching mechanism, 42 is a seal portion, 45 is a cartridge accumulation unit, 46 is a winding mechanism unit, 51 is a filter holder opening portion, 52 is a preheating unit, and 106 is a control unit.

Hereinafter, operation of Embodiment 8 of the invention will be described. Because a configuration and the operation of Embodiment 8 are similar to those of Embodiment 7, a different between both embodiments will be mainly described herein.

In Embodiment 8, the sheet-like filter cartridge 1 is received in the cartridge accumulation unit 45 in a state in which the sheet-like filter cartridge 1 has not been wound but has been folded in advance. Filter replacement operation is performed by moving the filter cartridge 1 forward by operation of the winding mechanism unit 46, successively drawing out the filter cartridge 1 from the cartridge accumulation unit 45, and positioning a new filter 2 in the filter holder opening portion 51. Further, used filter cartridges are successively collected by the cartridge collection portion 33. That is, in the case of filter replacement, the control unit 106 lowers the vertical motion sandwiching mechanism 41 to loosen the seal portion 42 and then operates the winding mechanism unit 46 to position a new unused filter 2 in the filter holder opening portion 51. Subsequently, the control unit 106 raises the vertical motion sandwiching mechanism 41 and sandwiches and seals the filter cartridge 1 by using the seal portion 42. Thus, the filter replacement is completed. In order to satisfactorily perform sealing, it is preferable that the plurality of filters 2 be provided in the filter cartridge 1 so as to have a gap between adjacent filters and, at the time of sealing, sealing be performed by inserting the seal portion 42 provided in the filter holder 3 into the gap.

As described above, because the form of the filter cartridge is a foldable sheet-like shape, space saving and reduction in costs can be achieved.

(I) Embodiment 9

Figure 19:
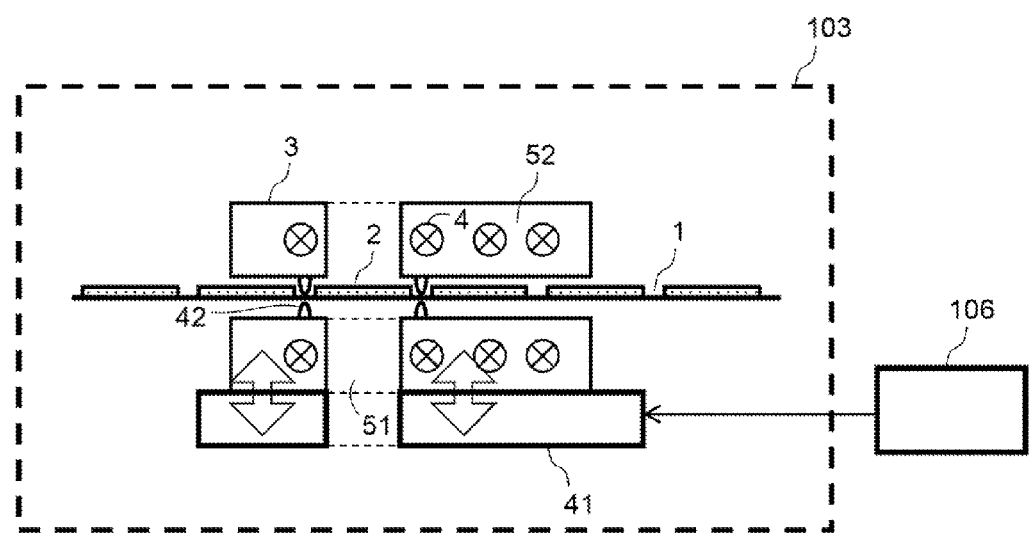
FIG. 19 is a cross-sectional schematic diagram of a configuration example of a thermal vaporization unit of a particle analyzing apparatus according to the invention.
Figure 20:
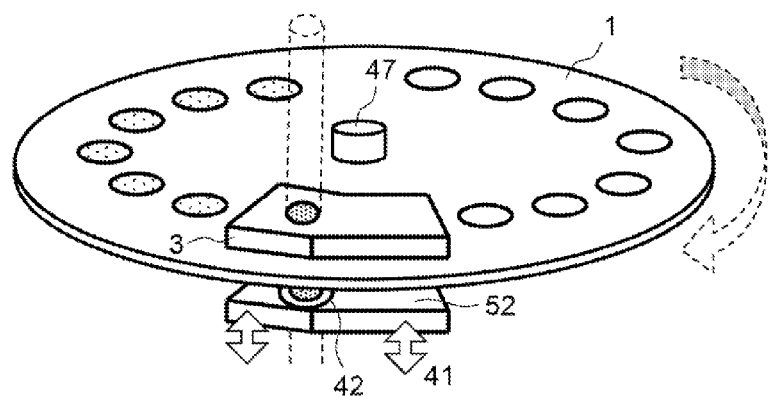
FIG. 20 is a perspective view of the configuration example of the thermal vaporization unit of the particle analyzing apparatus according to the invention.

FIGS. 19 and 20 illustrate Embodiment 9 of the invention. FIG. 19 is a cross-sectional schematic diagram of a thermal vaporization unit 103 of a particle analyzing apparatus according to this embodiment, and FIG. 20 is a perspective view thereof.

In FIGS. 19 and 20, 1 is a filter cartridge, 2 is a filter, 3 is a filter holder, 4 is a heater, 41 is a vertical motion sandwiching mechanism, 42 is a seal portion, 47 is a filter rotation mechanism, 51 is a filter holder opening portion, 52 is a preheating unit, and 106 is a control unit.

Hereinafter, operation of Embodiment 9 of the invention will be described. Because a configuration and the operation of Embodiment 9 are similar to those of Embodiment 8, a different between both embodiments will be mainly described herein.

In Embodiment 9, the filter cartridge 1 has a disk-shaped structure. The filter cartridge 1 is rotated by the filter rotation mechanism 47 under control of the control unit 106, and, with this, an unused filter is positioned with respect to the filter holder 3 and filter replacement operation is performed. A plurality of filters are provided in the filter cartridge 1 in a circumferential direction thereof. A filter to be used next is heated to have an appropriate temperature in advance in the preheating unit 52, thereby reducing a downtime at the time of filter replacement. In the case of filter replacement, the control unit 106 lowers the vertical motion sandwiching mechanism 41 to loosen the seal portion 42, and drives the filter rotation mechanism 47 to position the next unused filter 2 in the filter holder opening portion 51. Subsequently, the control unit 106 raises the vertical motion sandwiching mechanism 41 and sandwiches and seals the filter cartridge 1 by using the seal portion 42. Thus, the filter replacement is completed.

As described above, because the filter cartridge has the disk-shaped structure and the plurality of filters are provided in the circumferential direction, it is possible to simplify a mechanism for sending filters, improve reliability thereof, and reduce costs thereof.

In the present specification described above, for ease of description, each characteristic has been described as an individual embodiment. However, as a matter of course, some characteristics may be simultaneously implemented. In the present specification, the concentration unit, the gas analysis unit, and the like have not been described in detail. However, functions thereof can be achieved by existing technologies, respectively. For example, a mass spectrometer or an ion mobility detector can be used as the gas analysis unit, and a cyclone classifier or the like can be used as the concentration unit.

Further, the invention is not limited to the above embodiments and includes various modification examples. For example, the above embodiments have been described in detail to easily understand the invention, and therefore the invention is not necessarily limited to the embodiments having all the configurations described above. Further, a part of a configuration of a certain embodiment can be replaced with a configuration of another embodiment, and a configuration of another embodiment can be added to a configuration of a certain embodiment. Further, another configuration can be added to, removed from, or replaced with a part of the configuration of each embodiment.

REFERENCE SIGNS LIST 1 filter cartridge
2 filter
3 filter holder
4 heater
5 male screw seal portion
6 female screw seal portion
7 bolt head portion
8 concentration unit
11 light source
12 photodetector
13 detection hole
21 halogen lamp heater
31 front surface fitting portion
32 back surface fitting portion
33 cartridge collection portion
41 vertical motion sandwiching mechanism
42 seal portion
43 delivery mechanism unit
44 winding mechanism unit
45 cartridge accumulation unit
46 winding mechanism unit
47 filter rotation mechanism
51 filter holder opening portion
52 preheating unit
61 sending unit
101 collection portion
102 exhausting unit
103 thermal vaporization unit
104 analysis unit
105 display operation unit
106 control unit

The invention claimed is:

1. A particle analyzing apparatus, comprising:
   a concentration unit for concentrating gas containing particles to be detected;
   a thermal vaporization unit for collecting the particles in the gas concentrated in the concentration unit and thermally vaporizing the particles; and
   an analysis unit for analyzing a sample thermally vaporized in the thermal vaporization unit,
   wherein the thermal vaporization unit includes a flow channel connecting the concentration unit and the analysis unit, a first filter loaded into the flow channel, a seal portion for sealing the periphery of the flow channel in a state in which the first filter is loaded, a heating unit for heating the first filter, a second filter which is located outside the flow channel and is to be loaded next into the flow channel, a preheating unit for heating the second filter, and a filter replacement mechanism for unloading the first filter from the flow channel and loading the second filter into the flow channel.

2. The particle analyzing apparatus according to claim 1, wherein the heating unit heats the first filter within a range of 200° C. to 250° C.

3. The particle analyzing apparatus according to claim 1, wherein the first filter and the second filter are incorporated in a filter cartridge for holding filters, and the filter replacement mechanism drives the filter cartridge to move the first filter and the second filter in a direction crossing the flow channel.

4. The particle analyzing apparatus according to claim 3, comprising
   a filter holder to which the filter cartridge is attached,
   wherein the flow channel is set in the filter holder.

5. The particle analyzing apparatus according to claim 4, wherein:
   the filter cartridge has a columnar shape and has an outer circumference in which a male screw is formed;
   the filter holder has a cylindrical hole and has an inner circumference in which a female screw is formed to be fitted to the male screw;
   the filter replacement mechanism is a mechanism for loading the male screw into the female screw to perform rotation and forward movement; and
   the seal portion performs sealing by engagement of the male screw with the female screw.

6. The particle analyzing apparatus according to claim 5, wherein a lead length of the male screw and a lead length the female screw are equal to a pitch distance of the plurality of filters held by the filter holder.

7. The particle analyzing apparatus according to claim 4, wherein:
   the filter holder has a driving mechanism for performing operation for sandwiching the filter cartridge; and
   the seal portion performs sealing by bringing the filter holder and the filter cartridge into contact with each other by the sandwiching operation of the driving mechanism.

8. The particle analyzing apparatus according to claim 4, wherein the heating unit and the preheating unit are integrally included in the filter holder and simultaneously heat the first filter and the second filter.

9. The particle analyzing apparatus according to claim 8, wherein a total length of the heating unit and the preheating unit is longer than a distance between centers of at least two filters held by the filter cartridge, and the filter holder is extended in a direction opposite to a sending direction of the filter cartridge.

10. The particle analyzing apparatus according to claim 1, wherein the preheating unit is independent from the heating unit, and the preheating unit heats the second filter to a higher temperature than a heating temperature of the first filter heated by the heating unit.

11. The panicle analyzing apparatus according to claim 10, wherein the preheating unit includes heaters with a higher density than a density of heaters in the heating unit.

12. The particle analyzing apparatus according to claim 10, wherein the preheating unit includes infrared radiation means.

13. The particle analyzing apparatus according to claim 3, wherein:
   the filter cartridge has a detection hole for position detection; and
   the filter replacement mechanism includes a light source and a photodetector and stops driving of the filter cartridge when light beams emitted from the light source pass through the detection hole of the filter cartridge and are detected by the photodetector.

14. The particle analyzing apparatus according to claim 13, wherein the detection hole is extended in a direction in parallel to surfaces of the filters.

15. The particle analyzing apparatus according to claim 3, wherein:
   the filter cartridge has a cutout portion for position detection; and
   the filter replacement mechanism includes a light source and a photodetector and stops driving of the filter cartridge when light beams emitted from the light source pass through the cutout portion of the filter cartridge and are detected by the photodetector.

* * * * *